(12) United States Patent
St. Pierre et al.

(10) Patent No.: US 11,857,506 B2
(45) Date of Patent: Jan. 2, 2024

(54) ADAPTABLE PHARMACEUTICAL COUNTING DEVICE, SYSTEM, AND ADAPTER

(71) Applicant: Capsa Solutions LLC, Portland, OR (US)

(72) Inventors: John David St. Pierre, Worthington, OH (US); Pablo Arias Martinez, Vernon Hills, IL (US); Rasmey Yim, Happy Valley, OR (US); Tomasz Adam Michalski, Canal Winchester, OH (US); David Alan Bickel, Reynoldburg, OH (US)

(73) Assignee: Capsa Solutions LLC, Portland, OR (US)

( * ) Notice: Subject to any disclaimer, the term of this patent is extended or adjusted under 35 U.S.C. 154(b) by 259 days.

(21) Appl. No.: 17/370,401

(22) Filed: Jul. 8, 2021

(65) Prior Publication Data
US 2023/0011165 A1    Jan. 12, 2023

(51) Int. Cl.
*A61J 7/02* (2006.01)
*B65B 57/14* (2006.01)
*A61J 7/00* (2006.01)
*G06F 3/14* (2006.01)
*G16H 20/13* (2018.01)
*G16H 40/20* (2018.01)

(52) U.S. Cl.
CPC .............. *A61J 7/02* (2013.01); *A61J 7/0076* (2013.01); *B65B 57/145* (2013.01); *G06F 3/14* (2013.01); *G16H 20/13* (2018.01); *G16H 40/20* (2018.01)

(58) Field of Classification Search
CPC ........................................................ A61J 7/02
See application file for complete search history.

(56) References Cited

U.S. PATENT DOCUMENTS

| 4,874,348 | A  | * | 10/1989 | Lafreniere | ............... | G07D 1/08 |
| | | | | | | 221/281 |
| 6,761,010 | B1 | * | 7/2004 | Gibson | ................. | A61J 7/0084 |
| | | | | | | 53/247 |
| 6,854,618 | B2 | * | 2/2005 | Harrold | ................ | B65D 50/045 |
| | | | | | | 221/25 |

(Continued)

OTHER PUBLICATIONS

Hero Health, Hero Pill Dispenser, Medication Manager, and Pill Organizer, screen shot of webpage, accessed Jun. 30, 2021, 17 pages.

(Continued)

*Primary Examiner* — Gene O Crawford
*Assistant Examiner* — Ayodeji T Ojofeitimi
(74) *Attorney, Agent, or Firm* — Standley Law Group LLP; Adam J. Smith; Jeffrey S. Standley (57) ABSTRACT

A system for adaptably collecting pharmaceuticals into various containers is provided. The system includes an automated pharmaceutical counting device with a loading portion for accepting the pharmaceuticals for counting, an exit portion for dispensing the pharmaceuticals, and a receiving area configured to interchangeably accommodate a bulk collection vessel and an adapter for an individual container for an individual prescription. The automated pharmaceutical counting device dispenses the pharmaceuticals through the exit portion and into an inserted one of the bulk collection vessel and the adapter.

22 Claims, 6 Drawing Sheets

(56) References Cited

U.S. PATENT DOCUMENTS

2015/0151898 A1* 6/2015 Desset-Brethes ....... G01F 11/24
221/206
2020/0129379 A1* 4/2020 Fukada .................... A61J 7/02

OTHER PUBLICATIONS

Rxcount Corporation, Rx Counting Fast and Accurate Pill Counting, information sheet, Jun. 30, 2021, 1 page.
Kirby Lester, KL1Plus Pharmacy Tablet Counter, screen shot of webpage, accessed Jun. 30, 2021, 2 pages.
Kirby Lester, KL1 Pharmacy Tablet Counter, screen shot of webpage, accessed Jun. 30, 2021, 2 pages.
Kirby Lester, KL1 Tablet Counter Compact and Accurate Counting Device, information sheet, accessed Jun. 30, 2021, 2 pages.
Capsahealthcare, Streamlined Counting Plus Verification Kirby Lester KL1/Plus, information sheet, 2016, 2 pages.
Rxcount, Rx-4 Automatic Tablet and Capsule Counter, screen shot of webpage, Jun. 30, 2021, 7 pages.

* cited by examiner

ADAPTABLE PHARMACEUTICAL COUNTING DEVICE, SYSTEM, AND ADAPTER

CROSS-REFERENCE TO RELATED APPLICATIONS

This application makes no priority claim.

TECHNICAL FIELD

Exemplary embodiments relate generally to systems for counting pharmaceuticals in an adaptable manner, such as to accommodate both a large collection vessel and an individual container, counting devices, adapter apparatuses, and methods related to the same.

BACKGROUND AND SUMMARY OF THE INVENTION

Pharmaceutical counting devices are known which count a number of pharmaceuticals, such as pills or tablets, passed therethrough. Examples of such counting devices include those available under the Kirby Lester® brand (e.g., KL1™ and KL1Plus™) from Capsa Solutions LLC (d/b/a Capsa Healthcare®) of Canal Winchester, OH (https://kirbylester.com/kirby-lester-products-and-technology.html). Such devices are typically used in conjunction with a bulk collection vessel to catch the pharmaceuticals passed through the device for counting. The pharmaceuticals captured by the bulk collection vessel are sometimes then poured into individual containers for an individual prescription. The individual containers may be configured to hold medication for an individual prescription. For example, without limitation, the individual containers may be selectively closeable, such as by way of a lid, cap, one or more child resistant packaging features, combinations thereof, or the like. The bulk collection vessel is relatively large and bulky compared to an individual container, such as a bottle or vial, and are generally open on at least one side. For example, without limitation, the bulk collection vessel may be configured to remain open on at least one side and may be configured to selectively hold amounts of medication greater than normally required for a single individual prescription. At least some known counting devices are unable to accommodate individual containers, or such use may result in some of the pharmaceuticals missing the individual container, which may lead to inaccurate counting. Even if able to be safely used, use of such individual containers may result in an inability to use certain automated counting reset or other features of the device which may rely on the size or shape of the bulk collection vessel for activation.

In certain circumstances, such as but not limited to counting of a relatively small number of pharmaceuticals, it may be desirable to use such individual containers to catch the counted pharmaceuticals. This may reduce the amount of time and effort required to fill prescriptions, for example, by eliminating the need to transfer the counted pharmaceuticals from the bulk collection vessel to an individual container for dispensing to a customer. However, in some circumstances it may still be desirable to use a bulk collection vessel. Therefore, what is needed is an adaptable pharmaceutical counting device for various counting situations.

An adaptable pharmaceutical counting device and related system and adapter are provided. The disclosed systems, devices, and apparatuses may be configured to permit filling individual containers directly from a pharmaceutical counting device while maintaining an ability to operate interchangeability with bulk collection vessels for alternate counting situations. The disclosed systems, devices, and apparatuses may be configured to provide one-handed, or no-handed at least at times, operation for loading an empty individual container and unloading a filled individual container. The disclosed systems, devices, and apparatuses may be configured to, in the same unloading motion, reset a counting sensor on the counting device, thereby maintaining high speed cycling of the individual containers for improved efficiency.

An adapter may be configured for placement into a receiving area of the counting device also designed to interchangeably accommodate the bulk collection vessel. Placement of the adapter within the receiving area may trigger a sensor of the counting device which may initiate and/or reset counting, such as by the size and/or shape of the adapter or one or more protrusions on the same. The counting device, in exemplary embodiments, may be configured to initiate and/or reset counting, or take other action (such as but not limited to storing count, pharmaceutical, user, and/or prescription information) upon detection of the adapter within the receiving area and/or detection of removal of the adapter from the receiving area. The sensor may be also triggered by insertion of the bulk collection vessel.

The adapter may comprise a collecting portion for catching pharmaceuticals dispensed from the counting device and directing the dispensed pharmaceuticals towards a central area. A loading area below the collecting portion may be configured to accommodate the individual containers at the central area. The adapter may comprise one or more gripping tabs configured to receive the individual containers below the collecting portion and mechanically engage the individual containers when so placed to temporarily secure the individual containers at the adapter in position to receive the collected pharmaceutics from the collecting portion. The adapter may comprise one or more stopping mechanisms, which may be biased in an expanded position to selectively secure the adapter within the receiving area by way of apertures in the guides for receiving the stopping mechanisms. The apertures may be sized to permit limited travel of the adapter so that the adapter may remain within the receiving area while a filled one of the individual containers is removed and a new, empty one of the individual containers is inserted. However, sufficient travel may be provided to activate/deactivate the sensor and reset the count. One or more magnets may be provided at the adapter for drawing the adapter into the receiving area and/or temporarily securing the adapter within the receiving area.

At least certain of the counting devices may be configured to update count information as pharmaceuticals are passed through the counting device, such as in substantially real-time. This may eliminate a need for preloading a larger collection of pharmaceuticals than are required for the particular counting need. For example, only the limited number of pharmaceuticals needed to fill a given prescription need be passed through the counting device, rather than needing to load more than what is needed for the given prescription and stopping the dispensing when the desired count is reached. Otherwise, it may be necessary to remove excess pharmaceuticals before initiating counting of a different type of pharmaceutical. This may permit faster interchange of different types of pharmaceuticals for counting by the counting device, such as for rapidly filling different prescriptions for different medications. However, in other exemplary embodiments, the counting devices may be configured to hold a pre-loaded collection or queue of pharmaceuticals to be counted.

Further features and advantages of the systems and methods disclosed herein, as well as the structure and operation of various aspects of the present disclosure, are described in detail below with reference to the accompanying figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Embodiments of the invention are described herein with reference to illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Referring to FIG. 1 through FIG. 13, a counting device 1 may comprise a loading portion 2. The loading portion 2 may be configured to accept various pharmaceuticals, such as but not limited to, tablets and/or pills of various size, shape, and/or type. The loading portion 2 may comprise a funnel, chute, or other device for gathering pharmaceuticals, such as by gravitational forces, poured or otherwise directed at the counting device 1, such as from a bulk container for processing. The counting device 1 may comprise an exit portion 5. The exit portion 5 may comprise a chute or other device for dispensing pharmaceuticals from the device 1 at a central area.

The counting device 1 may comprise a sensing module 3. The sensing module 3 may be configured to count, identify, track and/or otherwise interact with pharmaceuticals passed through the counting device 1 by known techniques and may comprise one or more known components for performing the same. In exemplary embodiments, the sensing module 3 may comprise one or more sensors 28 internal to a housing 29 for the device 1. The counting module 3, or components thereof, may be interposed between, or form part of, the loading portion 2 and/or the exit portion 5.

The counting device 1 may comprise a display or interface 4 configured to display certain information about the pharmaceuticals counted by the count sensing module 3, such as the number and/or type of pharmaceuticals passed through the device 1, and/or accept user input regarding such counting or other functions of the device 1. The device 1 may comprise a receiving area 6. The receiving area 6 may comprise one or more surfaces, which may be flat or substantially flat, for interchangeably receiving a particular or various types of bulk collection vessels 7 and/or an adapter 9 placed thereon.

In exemplary embodiments, the counting device 1 may be configured to update count information displayed at the display or interface 4 as the pharmaceuticals are passed through the counting device 1, such as in substantially real-time. This may eliminate a need for preloading a larger collection of pharmaceuticals than are required for the immediate counting need. For example, only the limited number of pharmaceuticals needed to fill a given prescription need be passed through the counting device 1, rather than needing to load more than what is needed for the given prescription and stopping the dispensing when the desired count is reached. This may permit faster interchange of different types of pharmaceuticals for counting by the counting device 1, such as for rapidly filling different prescriptions for different medications. However, in other exemplary embodiments, the counting device 1 may be configured to hold a pre-loaded collection or queue of pharmaceuticals to be counted, such as in a tube, funnel, tray, chamber, combinations thereof, or the like.

Figure 1:
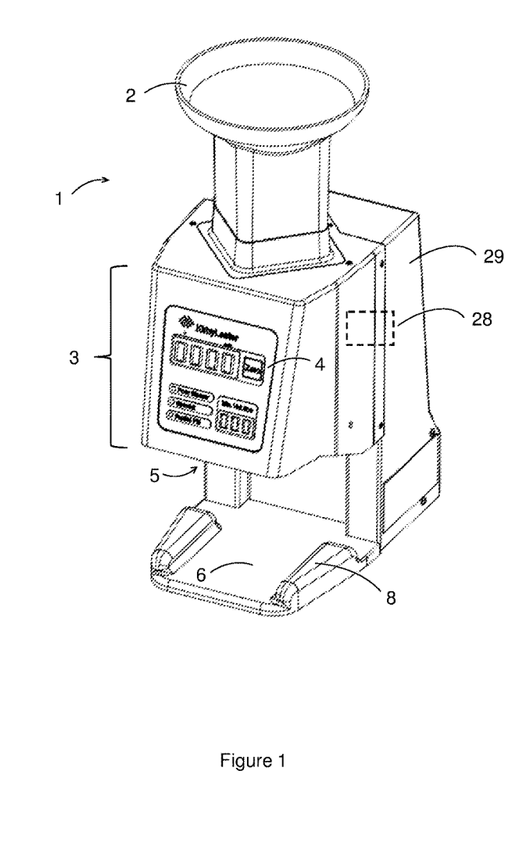
FIG. 1 is a front perspective view of an exemplary counting device.
Figure 2:
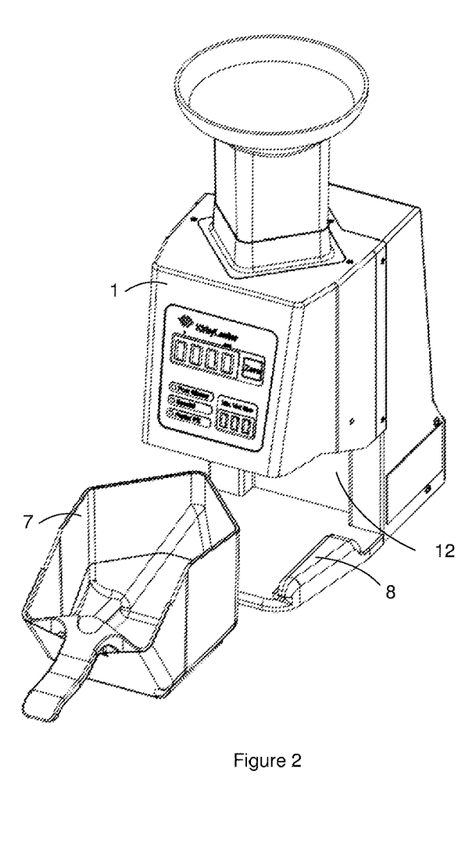
FIG. 2 illustrates the counting device of FIG. 1 with an exemplary bulk collection vessel being inserted.

As shown with particular regard to at least FIG. 2, the bulk collection vessel 7 may comprise a handle and a generally scoop shaped collection portion. The bulk collection vessel 7 may be configured to accommodate a relatively large number of pharmaceuticals. The bulk collection vessel 7 may be open on at least one side, such as the top, for receiving the pharmaceuticals dispended through the exit area 5 of the device 1. The bulk collection vessel 7 may define a volume necessary for relatively large volume counting, such as compared to an individual container 10. In exemplary embodiments, without limitation, the individual container 10 may be selectively closeable, such as by way of a lid, cap, one or more child resistant packaging features, combinations thereof, or the like. Alternatively, or additionally, the individual container 10 may be sized to hold medication for a single prescription. The bulk collection vessel 7 may be used for calibration of the counting device 1, by way of non-limiting example, where more pharmaceuticals need to be counted than are normally accommodated by an individual container 10. By way of other non-limiting examples, the bulk collection vessel 7 may be used for fulfilling larger prescriptions, checking inventory, quality control tests, combinations thereof, or the like. In exemplary embodiments, without limitation, the bulk collection vessel 7 may be configured to remain open on at least one side thereof. Alternatively, or additionally, the bulk collection vessel 7 may be sized to accommodate more medication than normally required to fill a single prescription.

The receiving area 6 may comprise one or more guides 8 configured to direct the bulk collection vessel 7 towards the exit portion 5 when the bulk collection vessel 7 is inserted into the receiving area 6. The guides 8 may comprise raised surfaces, angular surfaces, rails, high friction surfaces, combinations thereof, or the like.

Figure 3:
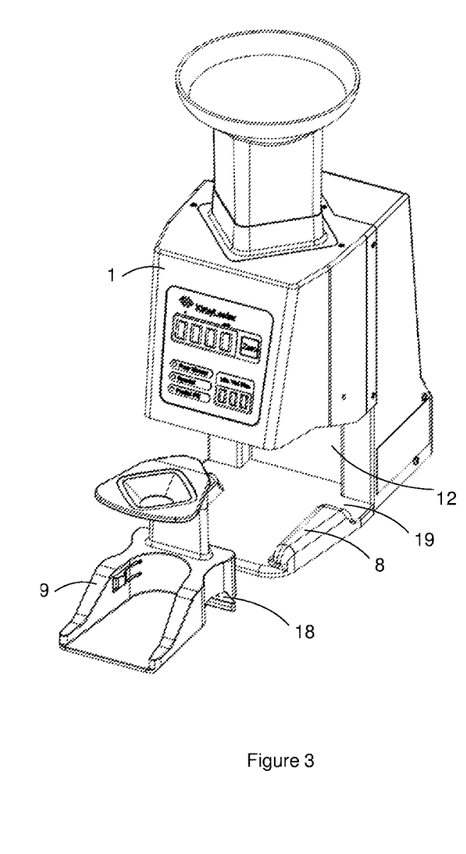
FIG. 3 illustrates the counting device of FIG. 1 with an exemplary adapter being inserted.

As shown with particular regard to at least FIG. 3, the receiving area 6 may be configured to interchangeably accommodate the adapter 9. The guides 8 may be configured to interchangeably receive the adapter 9 and direct the adapter 9 towards the exit portion when the adapter 9 is inserted into the receiving area 6. While interchangeability is described in some places herein, the device 1 may be configured to accommodate only the bulk collection vessel 7 or the adapter 9 in other embodiments.

The adapter 9 may be configured to accommodate one or more standard or non-standard size and/or type of individual containers 10. The adapter 9 may be used to fill individual prescriptions, by way of non-limiting example. The adapter 9 may comprise a loading area 11. The loading area 11 may comprise one or more surfaces, which may be substantially flat, for accommodating one of the individual containers 10 placed thereon. The adapter 9 may comprise one or more walls 30 extending upward from the loading area 11 to guide and/or stabilize individual containers 10 placed within the loading area 11, particularly while slid backwards into the adapter 9. Protrusions, surface features, or other objects for guiding, arresting movement of, or stabilizing the individual containers 10 within the loading area 11 may be utilized in addition to, or in lieu of, the walls 30. In exemplary embodiments, the one or more walls 30 may comprise a unitary wall forming a generally U or horseshoe shape about the loading area 11 to define an entrance area and forming a rear surface for arresting further movement of, and stabilizing, the individual container 10 when placed in the loading area 11 and slid rearward.

As shown with particular regard to FIGS. 8-12, the adapter 9 may comprise one or more stopping mechanisms 18. In exemplary embodiments, the stopping mechanisms 18 may be located on opposing sides of the adapter 9, though any number and placement of such stopping mechanisms 18 may be utilized. The stopping mechanisms 18 may be configured to be selectively depressed inward, such as by the guides 8 as the adapter 9 is inserted within the receiving area 6 and moved rearwards towards the exit area 5. The guides 8 may comprise or at least partially define one or more apertures 19 configured to permit the stopping mechanisms 18 to extend outward from the adapter 9 upon positioning of the adapter 9 in the receiving area 6 at the exit portion 5. In exemplary embodiments, the stopping mechanisms 18 may be configured to a fully or partially retracted position, such as where the stopping mechanisms 18 are located fully or partially within the one or more walls 30 of the adapter 9 when the adapter 9 is initially placed within the receiving area 6 and at least part of the time the adapter 9 is slid rearward within the receiving area 6, such as until the apertures 19 are reached. A number of apertures 19 may be provided in direct correlation to the number of stopping mechanisms 18 in exemplary embodiments, though such is not required.

When in an extended position, the stopping mechanisms 18 may protrude outwardly, such as beyond the wall(s) 30 of the adapter 9. The adapter 9 may comprise one or more apertures 31 in the wall(s) 30 configured to permit such movement of the stopping mechanisms 18.

The stopping mechanisms 18 may be biased into the extended position, such as by way of springs 24. In this way, when the adapter 9 is positioned such that the stopping mechanisms 18 align with the apertures 19, such as but not limited to when the adapter 9 is positioned below the exit portion 5, the stopping mechanisms 18 may be automatically extended into the apertures 19 to secure the adapter 9 in proper position within the receiving area 6. The stopping mechanisms 18 may be manually manipulated into the fully or partially retracted position for removal of the adapter 9 from the device 1. Alternatively, or additionally, the adapter 9 may be vertically lifted to disengage the stopping mechanism 18 from the device 1 for removal of the adapter 9. In other exemplary embodiments, without limitation, the stopping mechanism 18 may be connected to a button, lever, gear, or the like, actuation of which may fully or partially retract the stopping mechanisms 18.

Figure 4:
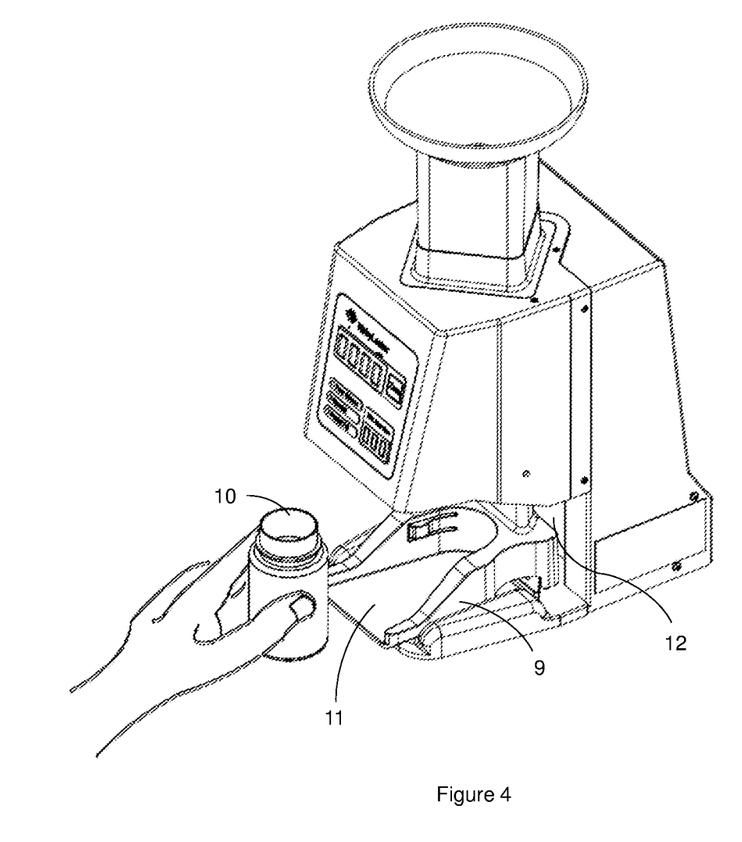
FIG. 4 is a side perspective view of FIG. 3 with an exemplary individual container being inserted into the adapter.
Figure 5:
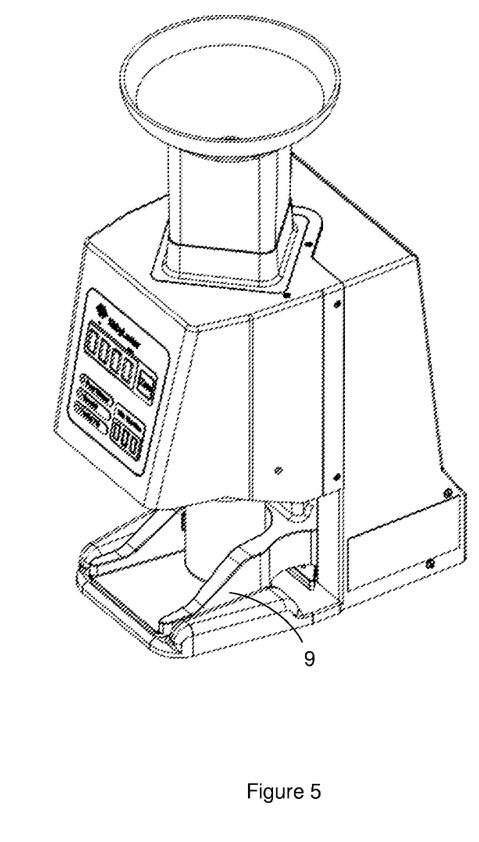
FIG. 5 illustrates the counting device of FIG. 4 with the individual container inserted into the adapter.
Figure 6:
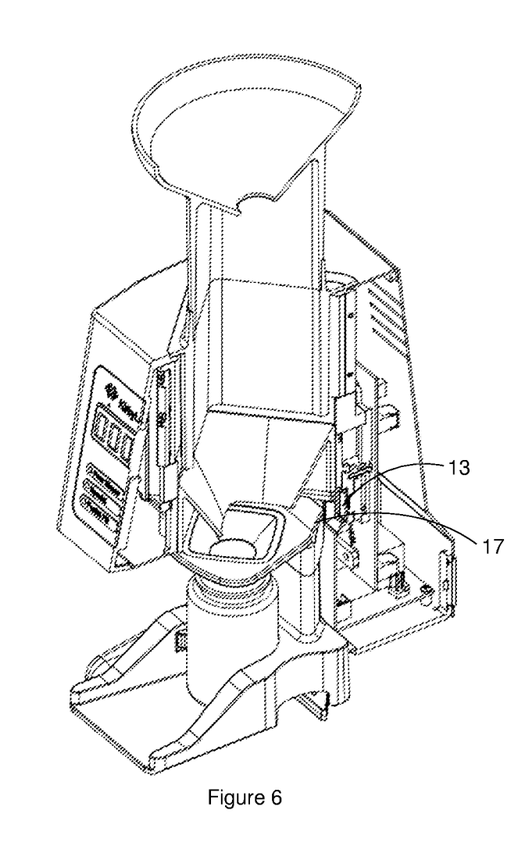
FIG. 6 is a partial sectional view of FIG. 5 with the counting device sectioned and the adapter in a forward position.
Figure 7:
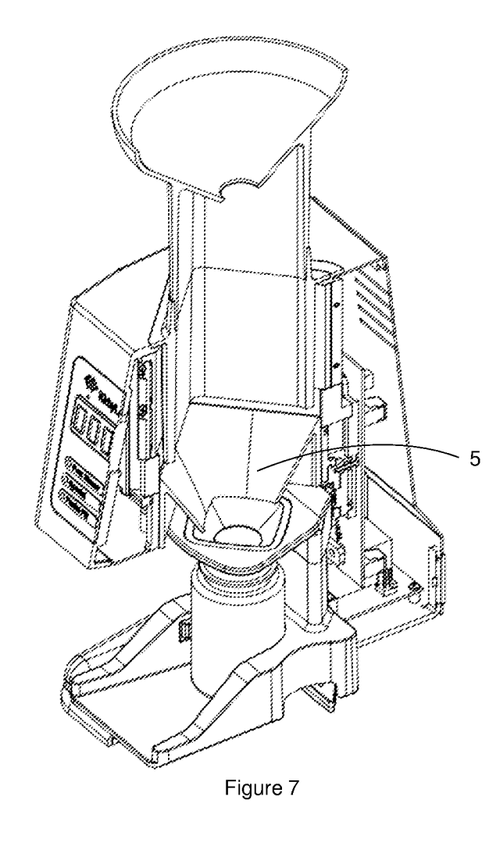
FIG. 7 illustrates the counting device, adapter, and individual container of FIG. 6 with the adapter in a rearward position.
Figure 8:
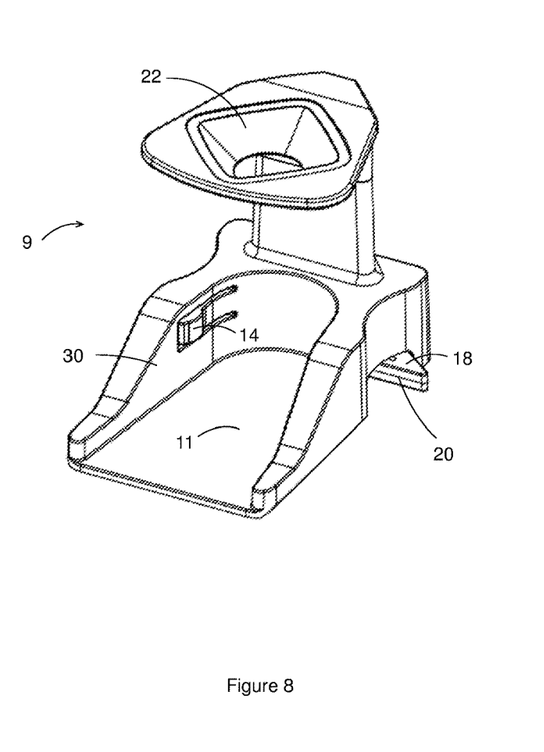
FIG. 8 is an isolated front perspective view of the adapter of FIG. 3.

The stopping mechanisms 18 may be attached to the adapter 9, such as at a rear surface 20 thereof. In exemplary embodiments, without limitation, the stopping mechanism 18 may be configured to accommodate screws 25 which pass therethrough for securing the stopping mechanisms to corresponding threaded apertures in the adapter 9, which may be located at the wall(s) 30. The apertures 19 and/or the stopping mechanisms 18 may be configured to permit limited travel of the adapter 9 within the receiving area 6 in exemplary embodiments, though such is not required. In this manner, forward pull of the adapter 9 within the receiving area 6 may be limited by the stopping mechanisms 18 and/or the apertures 19. FIGS. 4 and 6 illustrate the adapter 9 in a maximum forward position with the stopping mechanism 18 engaging the guides 8. FIGS. 5 and 7 illustrates the adapter 9 in a maximum rearward position with the adapter 9 engaging the device 1.

As shown with particular regard to FIGS. 4-5, the individual container 10 may be removably received within the adapter 9, such as by one-handed, or no-handed at least at times, operation of a user. The individual container 10 may be empty upon insertion into the adapter 9. The entry may be flat and low in the adapter 9, such as just above a table surface, which may permit short and convenient travel distances from the table surface to the loading area 11. The ergonomically positioned entry from the table surface to the loading area 11, which may be only slightly higher, may limit and prevent possible drops or spills of the individual container 10. As the individual container 10 is inserted into the adapter 9, the individual container 10 may be moved rearward within the loading area 11 and may engage with the adapter 9, such as at the wall(s) 30 and/or the gripping tabs 14. As this insertion motion continues, which may be singular and continuous in exemplary embodiments, the adapter 9 may contact an inside vertical wall 12 of the device 1, such as shown in FIGS. 5 and 7 by way of non-limiting example. The inside vertical wall 12 may arrest further rearward movement of the adapter 9 and/or the individual container 10. Maximum, or near maximum, rearward placement, such as shown in FIGS. 5 and 7, of the adapter 9 may trigger a sensor 13 of the device 1, such as shown in FIG. 6 for example without limitation. The sensor 13 may comprise an infrared proximity sensor in exemplary embodiments, though any other type of kind of sensor, or combination of sensors, may be utilized such as, but not limited to, ultrasonic sensors, light sensors, photo eyes, buttons, and switches to name some examples without limitation. Any number and kind of sensors 13 may be utilized and may be in electronic communication with the display or interface 4 in exemplary embodiments.

In exemplary embodiments, the apertures 19 may be sized to permit sufficient movement of the adapter 9 within the receiving area 6 for activating/deactivating the sensor 13, such as to reset a count performed by the device 1 by way of non-limiting example. In the maximum, or near maximum, forward pull, such as illustrated in FIGS. 4 and 6, the sensor 13 may not register a presence of the adapter 9 such that the count is reset. Alternatively, the machine 1 may be configured to reset the count upon detection of the presence of the adapter 9, bulk collection vessel 7, or other object in sensing range of the sensor 13. Such detection may occur at maximum, or near maximum, rearward push of the adapter 9, such as illustrated in FIGS. 5 and 7. In this manner, the count may be reset without the need for fully removing the adapter 9 from the device 1. However, the arrested motion of the adapter 9 by the stopping mechanism 18 may be sufficient to permit removal of the individual container 10 from the adapter 9, such as by removing the individual container 10 from the gripping tabs 14. For example, without limitation, the frictional forces exerted by the stopping mechanism 18 against the guides 8 may be greater than the force threshold required to remove the individual container 10 from the gripping tabs 14. The device 1 may be configured to provide one or more visual and/or audible signals upon activation of the sensor(s) 13, such as but not limited to at the display or interface 4. The device 1 may be configured to indicate a new, reset, and/or zeroed count on the display or interface 4 upon activation and/or deactivation of the sensor(s) 13. The device 1 may be configured to undertake such operation(s) upon readings form the sensor(s) 13 that the adapter 9 or bulk collection vessel 7 is inserted and/or removed.

The counting and obtaining of other information by the device 1 regarding the pharmaceuticals passing through the device 1 may be performed at the counting module 3 by the sensor(s) 28 which may comprise one or more known components and/or utilize one or more known techniques to accomplish such counting. The counting module 3 may comprise one or more controllers or other data processing equipment for collecting the information from the sensor(s) 28 and causing the information to be displayed at the display or interface 4, receiving user input at the display or interface 4 and updating device 1 function accordingly, and/or receiving information from the sensor(s) 13 and resetting the count or other information.

Completed full rearward motion of the adapter 9 may engage the individual container 10 into one or more gripping tabs 14, which may be provided at the adapter 9 and may be configured to temporarily secure the individual container 10 within the adapter 9.

One or more magnets 15 may be provided at the adapter 9, such as but not limited to at the inside vertical wall 12. The magnet(s) 15 may be configured to draw the adapter 9 rearward and/or maintain a position of the adapter 9 within the receiving area 6 by magnetic forces. One or more corresponding magnets or items of a ferrous nature may be provided at the device 1, such as at the inside vertical wall 12, to so engage the magnet(s) 15 of the adapter 9 and/or the housing or other components of the device 1 may comprise one or more ferrous material for engaging the magnet(s) 15. The bulk collection vessels 7 may likewise comprise such magnets. Alternatively, or additionally, the adapter 9 and/or bulk collection vessels 7 may comprise items of a ferrous nature and/or ferrous materials and the device 1 may comprise magnet(s).

The adapter 9 may comprise one or more protrusions 17 positioned to ensure activation of one or more of the sensor(s) 13 upon insertion of the adapter 9 and centering of the individual container 10 under the exit portion 5 during the filling/counting process. These protrusions 17 may be configured to account for the relatively small and/or different size of the adapter 9 compared to the bulk collection vessel 7.

When utilizing the adapter 9 with the device 1, the user may keep his or her hand on the individual container 10 within the adapter 9 while pouring the pharmaceutical (e.g., tablets, pills), such as for an individual prescription for example without limitation, into the loading portion 2 with his or her other hand, thereby providing an efficient workflow. During the filling/counting process, the display or interface 4 may be configured to indicate a count of the pharmaceutical to the user. The device 1 may be configured to update the count as such pharmaceuticals pass through the device 1 and are counted by the sensor(s) 28, such as in substantially real time. When the desired count is reached, the user may cease providing the pharmaceuticals at the loading portion 2, and may pull the individual container 10 forward. Upon application of sufficient force by the user, the magnet(s) 15, to the extent utilized, may disengage the adapter 9, which may be released from the rearward position for forward travel until the stopping mechanism 18 contact the guides 8. In exemplary embodiments, the grip tabs 14 on the adapter 9 may continue to hold the individual container 10 upon disengagement of the adapter 9 with the device 1 so that the individual container 10 and adapter 9 move forward as a single unit until the two stopping mechanisms 18 of the adapter 9 reach an end of the apertures 19 and engage the guides 8. Upon application of continued or further force, the gripping tabs 14 may be configured to release individual container 10 from the adapter 9, which may now be filled with a desired amount of counted pharmaceuticals, such as in a smooth, continuous motion by the user. In this way, a new, empty individual container 10 may be inserted into the adapter 9 for filling by the device 1 without removing the adapter 9. The limited forward movement of the adapter 9 during interchange of the individual containers 10 may move the protrusion(s) 17 or other portion of the adapter 9 outside of the range of the sensor(s) 13. The device 1 may be configured to continue indication of the count of the last filling, such as by flashing, at the display or interface 4. This may complete a single filling process. The process may be repeated any number of times for any number of individual containers 10 and/or bulk container vessels 7 as descried by the user(s). This may be particularly useful to rapidly filling multiple prescriptions, by way of non-limiting example.

When finished with the adapter 9, the user may manually move the stopping mechanisms 18 into a retracted position so that the stopping mechanisms 18 no longer engage the guides 8, permitting removal of the adapter from the device 1. When in the retracted position, the stopping mechanisms 18 may extend within wall(s) 30 of the adapter 9, for example without limitation.

With particular regard to FIGS. 6-7, the exit portion 5 may comprise one or more sloped sides, which may be cross-sectionally parabolic in shape, to facilitate desirable trajectory for the pharmaceuticals toward a centerline axis of the individual container 10. With particular regard to FIG. 8, the adapter 9 may comprise a collecting portion 22. The collecting portion 22 may comprise a funnel, chute, or other device for gathering pharmaceuticals from the exit portion 5 and directing them towards the individual container 10. The collecting portion 22 may comprise a softer material (e.g., as determined by a durometer) relative to the exit portion 5 so as to dampen a speed of pharmaceuticals and further direct the trajectory of the pharmaceuticals to the individual container 10.

Figure 9:
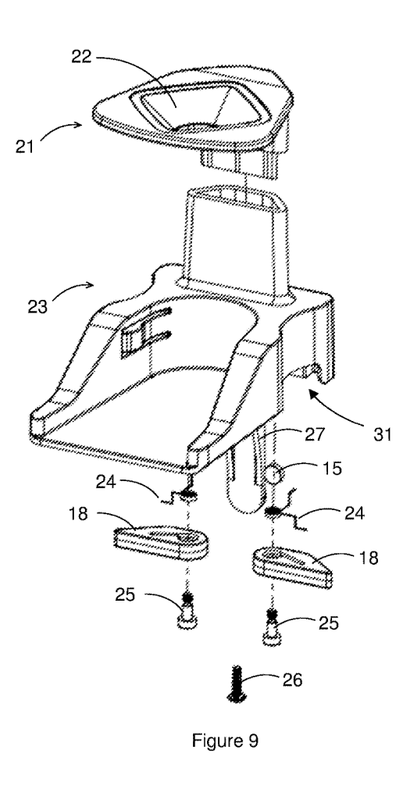
FIG. 9 is an exploded view of the adapter of FIG. 8.
Figure 10:
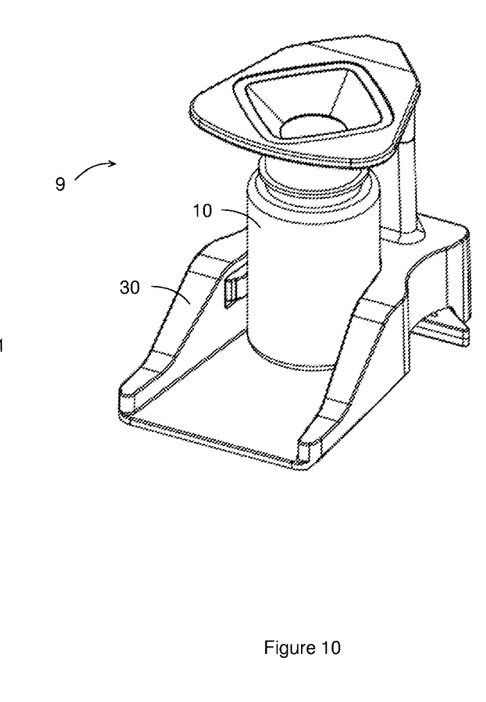
FIG. 10 illustrates the adapter of FIG. 8 with the individual container inserted.
Figure 11:
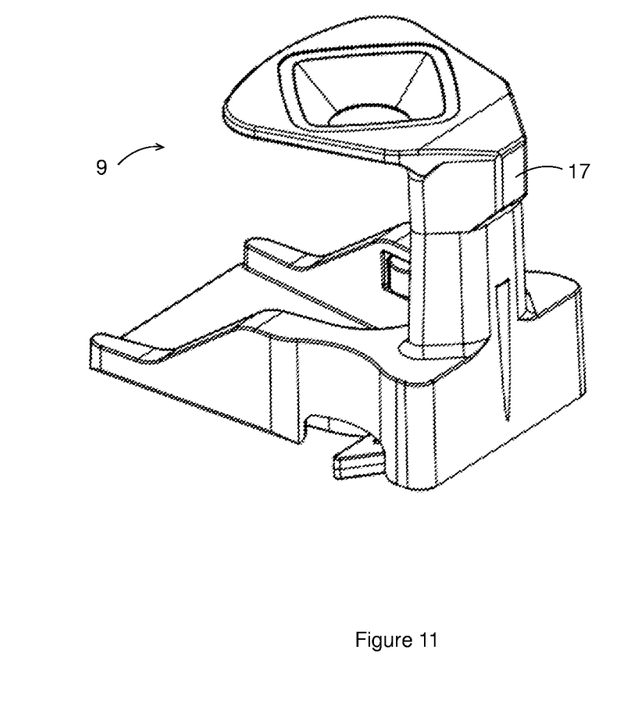
FIG. 11 is a rear perspective view of the adapter of FIG. 8.
Figure 12:
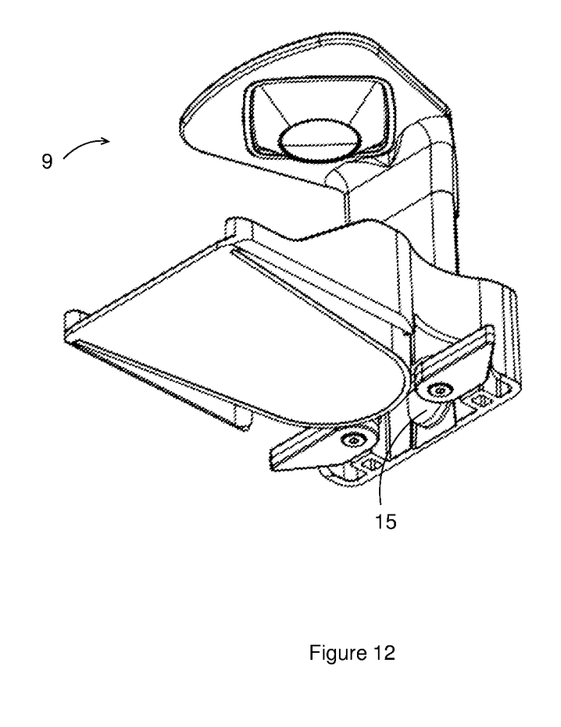
FIG. 12 a bottom perspective view of the adapter of FIG. 8.

With particular regard to FIG. 9, the adapter 9 may comprise an upper portion 21. The upper portion 21 may comprise the collecting portion 22. The adapter 9 may comprise a lower portion 23. The lower portion 23 may serve as a base configured to be received within the receiving area 6. The lower portion 23 may comprise the loading area 11 for the individual containers 10. The lower portion 23 may comprise one or more walls 30 for guiding the individual container 10 within the lower portion 23, such as to the gripping tabs 14, which may be located in such wall(s) 30. The lower portion 23 may be configured to mate with the upper portion 21, or the upper and lower portions 21 and 23 may be integrally formed.

The upper portion 21 may be sufficiently spaced from the lower portion 23 to accommodate standard size individual containers 10. The adapter 9 may be provided in various sizes and/or shapes to accommodate various size and/or shape individual containers 10. Alternatively, or additionally, the upper portion 21 may be moveable and/or selectively securable at a number of positions relative to the lower portion 23 to accommodate various size individual containers 10. In exemplary embodiments, the upper portion 21 may be selectively removable from the lower portion 23 so as to accommodate various size individual containers 10.

The adapter 9 may comprise one or more mounts 27 for the one or more magnets 15. The mount 27 may be connected to the lower portion 23 by way of one or more threaded fasteners 26 in exemplary embodiments. The stopping mechanisms 18 may each be configured to accommodate a spring 24, which may also engage a remaining portion of said adapter 9 such as to bias the stopping mechanism 18 in an extended position. The stopping mechanisms 18 and/or springs 24 may be attached to the lower portion 23 with screws 25, though such is not required. The stopping mechanisms 18 may comprise one or more recessed portions configured to accommodate some or all of the spring 24.

Various components of the adapter 9 may be integrally formed, permanently, or semi-permanently attached to one another, such as but not limited to by way of fasteners (threaded or otherwise), adhesive, snap fit, friction fit, welding, combinations thereof, or the like.

The individual container 10 may comprise a bottle, vial, or other container designed to hold a relatively small number of pharmaceuticals compared to the bulk collection vessel 7. In exemplary embodiments, the bulk collection vessel 7 may be configured to remain open at a top portion thereof, and the individual container 10 may be configured for selective closing, such as but not limited to by way of a safety cap, though such is not required. Any size, shape, or type individual container 10 may be utilized. Any size, shape, or type of bulk collection vessel 7 may be utilized. In exemplary embodiments, the individual container 10 is any container configured to hold an individual prescription of a patient and may adhere to one or more rules, regulation, or standards for such prescription containers, though such is not necessarily required. The bulk collection vessel 7 may comprise one or more sides or other features designed to permit pouring or other transfer of counted pharmaceuticals to the individual container 10, for example.

Figure 13:
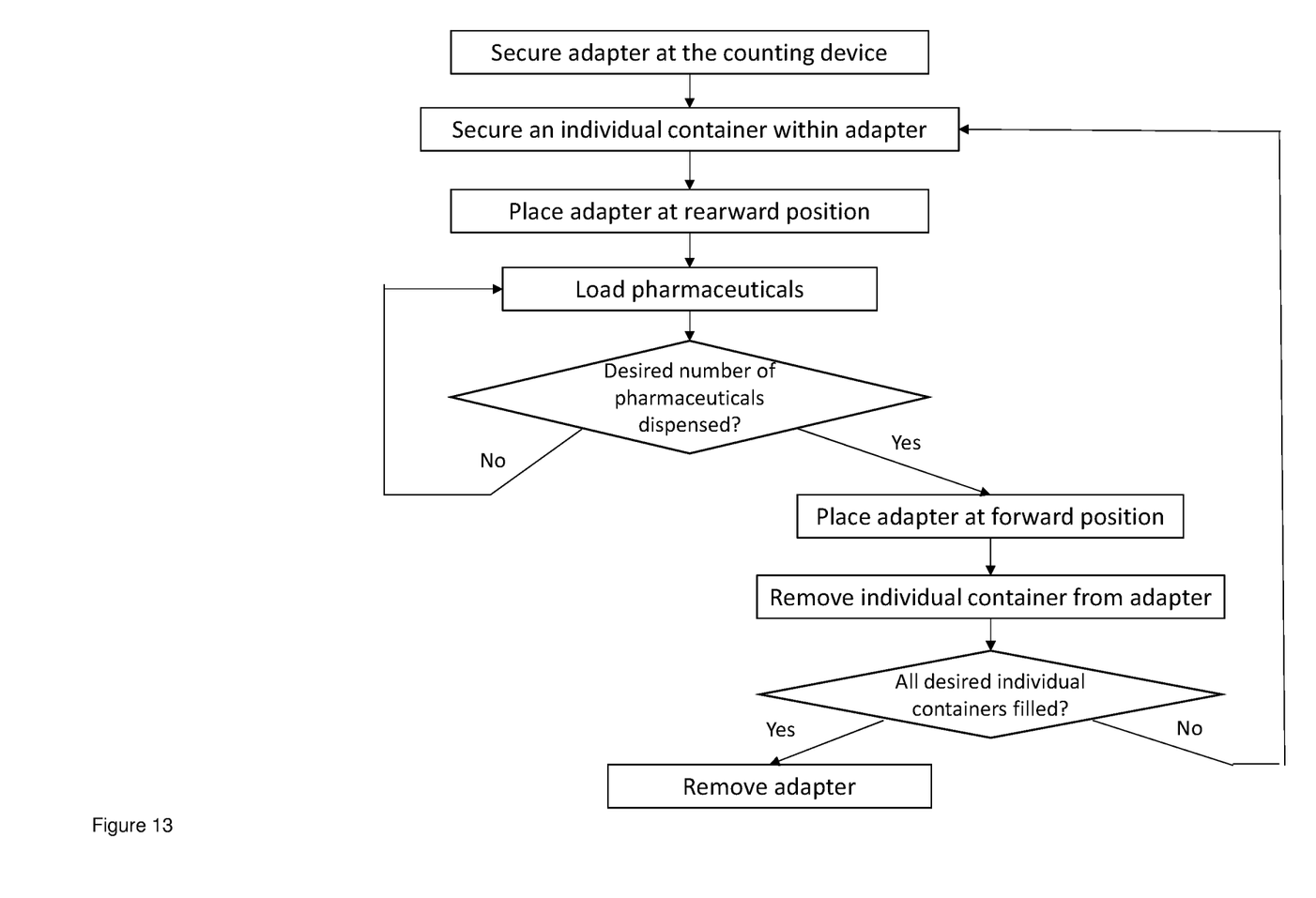
FIG. 13 is a flow chart with an exemplary workflow for utilizing the adapter with the counting device.

With particular regard to FIG. 13, exemplary workflows for operating the adapter 9 with the counting device 1 are provided. In exemplary embodiments, without limitation, the adapter 9 may be secured at the counting device 1, such as by engaging the stopping mechanism 18 within the apertures 19. An individual container 10 may be secured at the adapter 9, such as within the gripping tabs 14. The adapter 9 may be placed in a rearward position, such as where the protrusion 17 activates the sensor 13. The pharmaceuticals may be loaded into the device 1, such as for counting and dispensing into the individual container. Additional pharmaceuticals may be added until a desired number of pharmaceuticals is reached. The adapter 9 may be placed in the forward position, such as where the stopping mechanism 18 contact the guides 8 and the sensor 3 is no longer activated by the protrusion 17. The individual container 10 may be removed from the adapter 9. A new one of the individual containers 10 may be loaded into the adapter 9 and at least the steps of placing the adapter 9 in the rearward position, loading pharmaceuticals, placing the adapter 9 in the forward position, and removing the individual container 10 may be repeated any number of times until all desired individual containers 10 are filled. The adapter 9 may be removed once all desired individual containers 10 are filled, though such is not required.

Any of the steps may be completed in any order. For example, the individual container 10 may be secured within the adapter 9 before the adapter 9 is initially secured within the counting device 1. Any of the steps may be completed simultaneously or together. For example, the adapter 9 may be placed at the rearward position with the same motion that secures the individual container 10 within the adapter 9. As another example, the adapter 9 may be placed in the forward position with the same motion which removes the individual container 10 from the adapter 9. Any step or steps may be repeated any number of times. For example, any number of individual containers 10 may be filled. Any step or steps may be omitted. For example, once all desired individual containers 10 are filled, the adapter 9 may be left in the counting device 1 for later use. Alternatively, once the adapter 9 is removed, the bulk collection vessel 7 may be inserted, or the adapter 9 may be reinserted for continued counting activities. The desired number of pharmaceuticals may be loading during counting by the counting device 1 or may be pre-loaded for dispensing in a desired amount.

Any embodiment of the present invention may include any of the features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

Certain operations described herein may be performed by one or more electronic devices. Each electronic device may comprise one or more processors, electronic storage devices, executable software instructions, and the like configured to perform the operations described herein. The electronic devices may be general purpose computers or specialized computing device. The electronic devices may comprise personal computers, smartphones, tablets, databases, servers, or the like. The electronic connections and transmissions described herein may be accomplished by wired or wireless means. The computerized hardware, software, components, systems, steps, methods, and/or processes described herein may serve to improve the speed of the computerized hardware, software, systems, steps, methods, and/or processes described herein.

What is claimed is:

1. An adapter for an automated pharmaceutical counting device, said adapter comprising:
   an upper portion comprising a collecting portion configured to collect pharmaceuticals dispensed from the automated pharmaceutical counting device and direct said collected pharmaceuticals to a central area; and
   a lower portion configured to be removably inserted into a receiving area of said automated pharmaceutical counting device and comprising a loading area configured to removably receive a prescription vial configured to hold medication for an individual prescription at said central area for receiving said collected pharmaceuticals from said collecting portion;
   wherein a lower surface of the collecting portion is spaced apart from an upper surface of the loading area at a height sufficient to accommodate the prescription vial of a particular size.

2. The adapter of claim 1 wherein:
   said prescription vial is configured to be selectively closed and comprises one or more child resistant packaging features.

3. The adapter of claim 1 wherein:
   said upper portion is removable from the lower portion.

4. The adapter of claim 1 further comprising:
   one or more magnets configured to magnetically engage the automated pharmaceutical counting device when said adapter is placed within said receiving area.

5. The adapter of claim 1 further comprising:
   one or more gripping tabs positioned within the loading area of the lower portion to engage the prescription vial upon placement of the prescription vial within the loading area.

6. The adapter of claim 1 further comprising:
   one or more stopping mechanisms; and
   one or more springs, each engaging a respective one of the one or more stopping mechanisms and the lower portion to bias the respective one of the one or more stopping mechanisms in an extended position where the respective one of the one or more stopping mechanisms extends beyond an outer wall of the lower portion.

7. The adapter of claim 1 further comprising:
   a protrusion located at a rear surface of said adapter and configured to trigger a sensor located at the pharmaceutical counting device upon placement of the adapter within the receiving area of said pharmaceutical counting device.

8. The adapter of claim 1 wherein:
   said collecting portion comprises a series of sloped walls.

9. A system for adaptably collecting pharmaceuticals into various containers, said system comprising:
   a bulk collection vessel;
   an adapter configured to receive an individual container configured to hold medication for an individual prescription; and
   an automated pharmaceutical counting device comprising:
      a loading portion configured to accept said pharmaceuticals for counting;
      an exit portion configured to dispense said pharmaceuticals; and
      a surface located below the exit portion and comprising one or more guides for directing an inserted one of said bulk collection vessel and said adapter into a position below the exit portion; and
   a receiving area defined at least in part by at least a portion of the surface and the one or more guides;
   wherein said bulk collection vessel and said adapter are configured to interchangeably and individually received at said receiving area to receive the pharmaceuticals dispensed through the exit portion and into said inserted one of the bulk collection vessel and the adapter.

10. The system of claim 9 further comprising:
    a magnet located at a rear surface of said adapter; and
    a magnet or ferrous material located at automated pharmaceutical counting device within or adjacent to said receiving area for engaging said magnet of said adapter upon insertion of said adapter within said receiving area.

11. The system of claim 9 wherein:
    said exit portion comprises a first chute comprising a first material of a first hardness;
    said adapter comprises a second chute comprising a second material of a second hardness; and
    said second material is softer than said first material.

12. The system of claim 9 wherein:
    said individual container comprises a vial configured to be selectively closed; and
    said bulk collection vessel comprises a scoop and is configured to remain open on at least one side.

13. The system of claim 9 further comprising:
    one or more sensors located at said automated pharmaceutical counting device for resetting a count of said pharmaceuticals upon detection of insertion or removal of either of said bulk collection vessel and said adapter;
    one or more stopping mechanisms located at said adapter, wherein each of said one or more stopping mechanisms are spring loaded to bias the one or more stopping mechanisms in an extended position where said one or more stopping mechanisms extends beyond outer sidewalls of said adapter, and wherein each of said one or more stopping mechanisms are configured to be selectively placed in a retracted position where said one or more stopping mechanisms extend within the sidewalls of the adapter; and
    an aperture located in or adjacent to each of said one or more guides configured to accommodate one of the one or more stopping mechanisms such that the one or more stopping mechanisms are extendable into the extended position when the adapter is placed within the receiving area so as to secure the adapter relative to the automated pharmaceutical counting device, wherein each of said apertures are sized to permit limited forward and rearward travel of said stopping mechanisms within said apertures so as to permit corresponding limited forward and rearward travel of said adapter within said receiving area before said stopping mechanisms engage said guides for activating and deactivating said one or more sensors.

14. The system of claim 13 wherein:
said adapter comprises a number of gripping tabs configured to temporarily secure said individual container within said adapter.

15. The system of claim 13 further comprising:
a display or interface located at the automated pharmaceutical counting device and in electrical communication with said one or more sensors, wherein said display or interface is configured to display information regarding the pharmaceuticals passing through the automated pharmaceutical counting device including the count.

16. The system of claim 13 further comprising:
a protrusion located at a rear surface of said adapter configured to activate or deactivate said one or more sensors upon placement of said adapter within said receiving area.

17. The system of claim 16 wherein:
said one or more sensors comprises an infrared proximity sensor.

18. An adaptable automated pharmaceutical counting device, said device comprising:
a loading portion configured to accept said pharmaceuticals for counting;
an exit portion configured to dispense said pharmaceuticals;
a loading surface;
one or more guides, each located at said loading surface for directing an inserted one of a bulk collection vessel and an adapter into a position below the exit portion; and
a receiving area defined at least in part by said loading surface and said one or more guides, said receiving area configured to interchangeably accommodate, one at a time, said bulk collection vessel and said adapter for an individual prescription vial.

19. The device of claim 18 wherein:
said individual container is configured to be selectively closed and comprises at least one child resistant packaging feature; and
said bulk collection vessel is configured to remain open on at least one side.

20. The device of claim 18 further comprising:
one or more apertures, each defined in part by a distal end of one of said one or more guides, wherein each of said one or more apertures are configured to accommodate one of one or more stopping mechanisms when extended from said adapter when the adapter is placed within the receiving area so as to secure the adapter relative to the automated pharmaceutical counting device and permit limited travel of said stopping mechanisms within said apertures so as to permit corresponding limited travel of said adapter within said receiving area before said stopping mechanisms engage said guides.

21. The device of claim 20 further comprising:
at least one proximity sensor configured to detect placement of either of said bulk collection vessel and said adapter within said receiving area;
a counting module comprising at least one counting sensor interposed between said loading portion and said exit portion and configured to count said pharmaceuticals passing through the device in a given session and a display or interface for displaying information about the count, wherein said counting module is in electronic communication with said at least one proximity sensor and is configured to reset said displayed information upon receipt of information from said at least one proximity sensor indicating that an inserted one of said bulk collection vessel and said adapter has been removed from said receiving area.

22. The device of claim 21 wherein:
said at least one sensor comprises an infrared proximity sensor located at an inside rear wall adjacent to said receiving area.

* * * * *